US00PP30276P2

(12) United States Plant Patent
Van Swieten

(10) Patent No.: US PP30,276 P2
(45) Date of Patent: Mar. 5, 2019

(54) ***PHALAENOPSIS* ORCHID PLANT NAMED 'PHALGYQAN'**

(50) Latin Name: ***Phalaenopsis* hybrid**
Varietal Denomination: PHALGYQAN

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,389

(22) Filed: Nov. 3, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGYQAN', particularly characterized by having small, light purple flowers with dark purple spots and a dark red-purple lip, with the intensity and number of spots dependent on the temperature, 1 to 3 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALGYQAN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGYQAN'.

The new *Phalaenopsis* plant is a product of a planned breeding program conducted by the inventor in Bleiswijk, The Netherlands. The objective of this breeding program was to create a new *Phalaenopsis* plant with numerous attractive and unique small, light purple flowers with dark purple spots and a dark red-purple lip, suitable for potted plant production.

The new *Phalaenopsis* plant 'PHALGYQAN' is a result of cross-pollination made by the inventor in August 2009 in Bleiswijk, The Netherlands of the proprietary female, or seed parent, *Phalaenopsis* hybrid '10692-03' (unpatented) with the proprietary male, or pollen parent, *Phalaenopsis* hybrid '01-2078' (unpatented).

The new *Phalaenopsis* was selected by the inventor as a single plant within the progeny of the stated cross-pollination in a controlled greenhouse in Bleiswijk, The Netherlands in July 2012. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGYQAN' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGYQAN' as a new and distinct variety of *Phalaenopsis* plant.

1) Small, light purple flowers with dark purple spots and a dark red-purple lip, with the intensity and number of spots dependent on the temperature;
2) 1 to 3 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in September 2017. Colors in the photographs may differ from the color values cited in the detailed botanical description, which accurately describe the actual colors of the new variety.

DESCRIPTION OF THE NEW VARIETY

Figure 1:
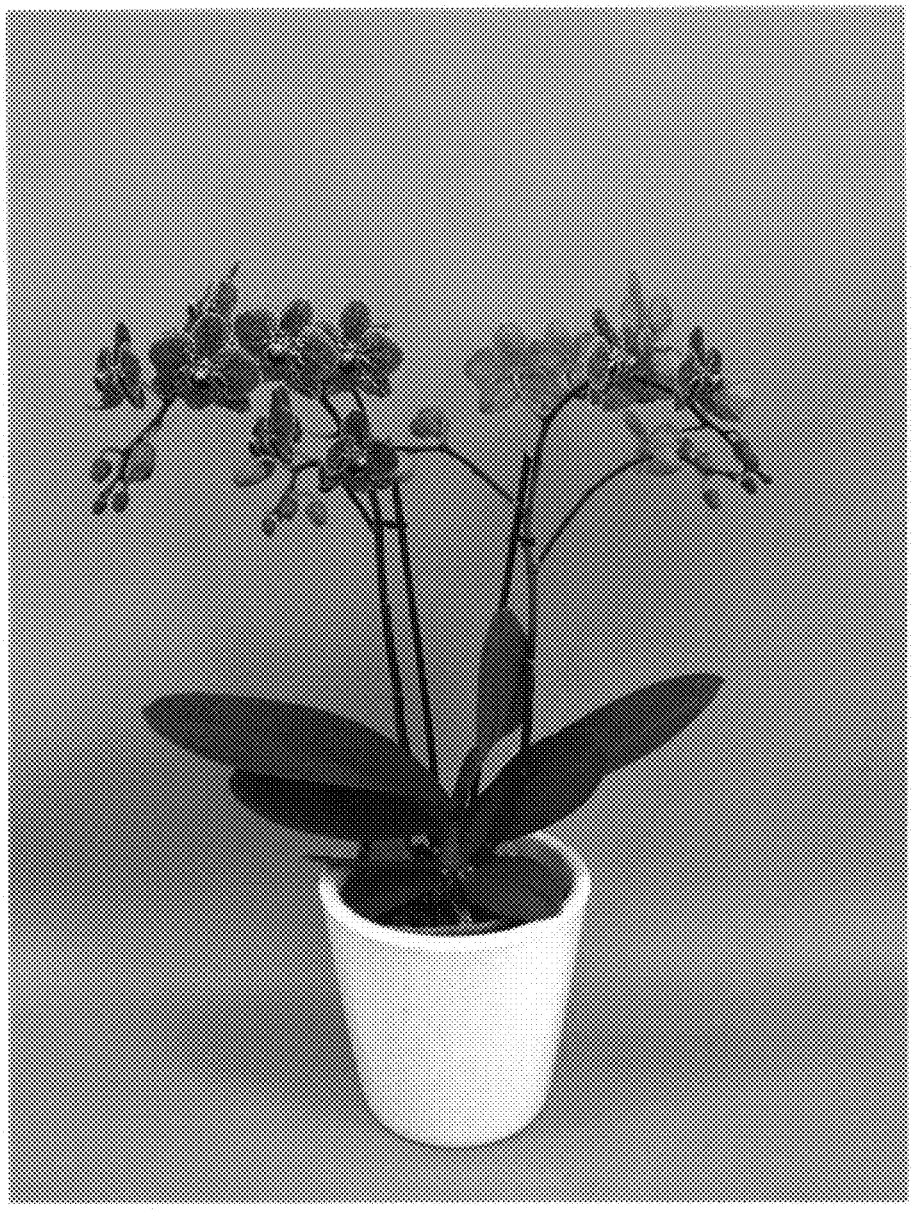
FIG. 1 shows the overall plant habit, including blooms, buds and foliage of 'PHALGYQAN'.
Figure 2:
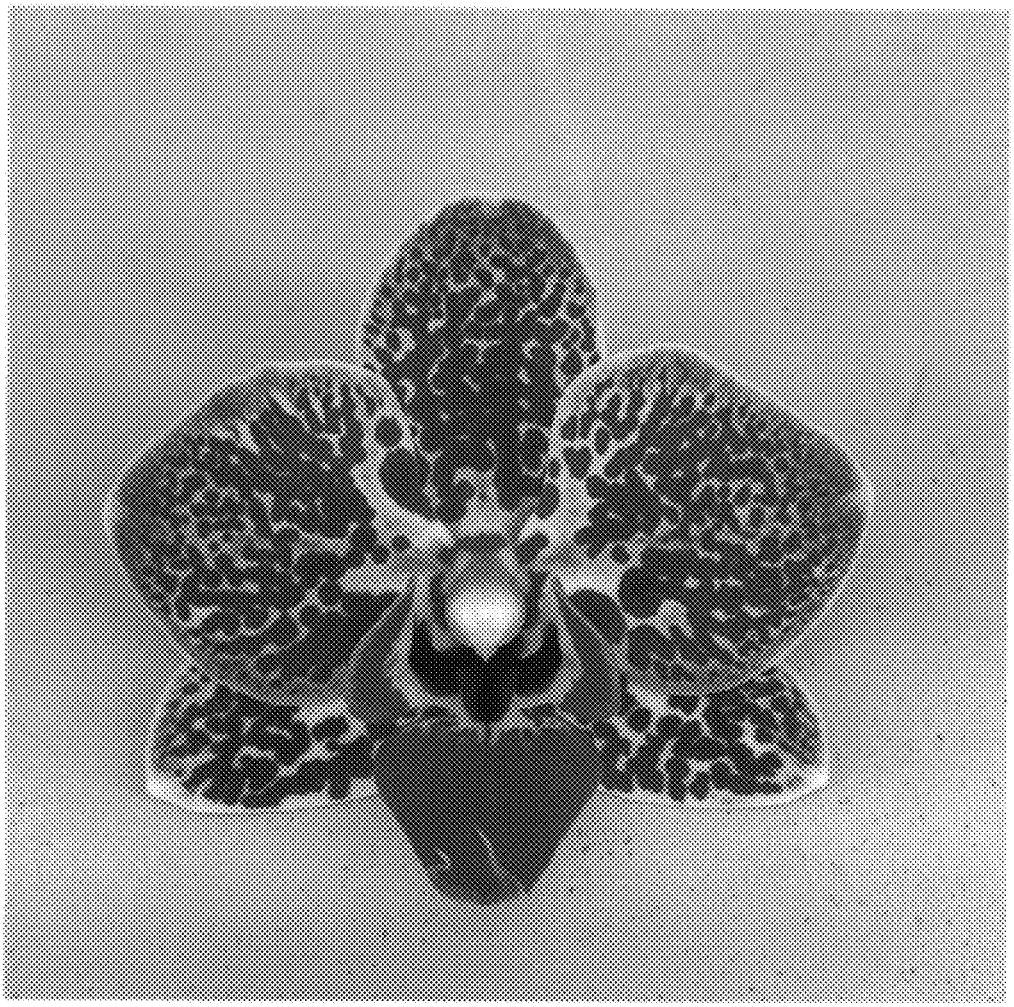
FIG. 2 shows a close-up of a flower of 'PHALGYQAN'.
Figure 3:
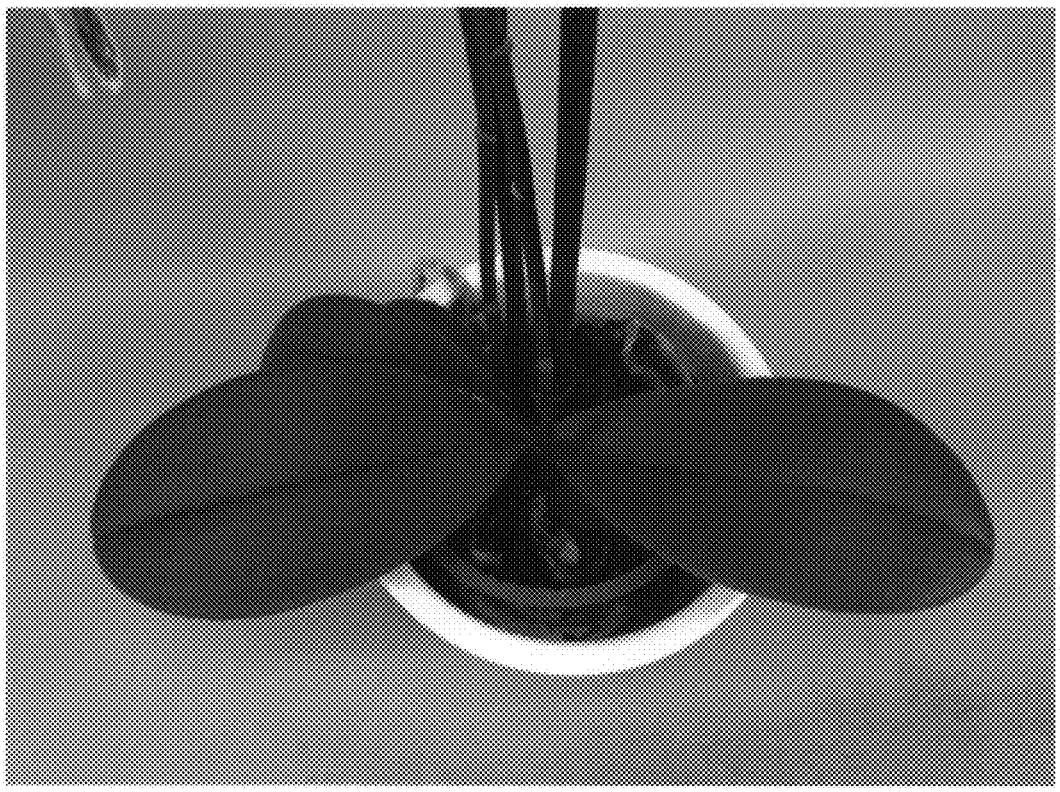
FIG. 3 shows a close-up of the leaves of 'PHALGYQAN'.

The following detailed description sets forth the distinctive characteristics of 'PHALGYQAN'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in September 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGYQAN'.

Parentage:

*Female parent*.—*Phalaenopsis* cultivar '10692-03' (unpatented).

*Male parent*.—*Phalaenopsis* cultivar '01-2078' (unpatented).

Propagation:

*Type*.—Meristem tissue culture.

Roots:

*Root description*.—Greyed-green colored roots (RHS 190B/C) with branching lateral roots having red-purple colored root tips (RHS N79B).

Plant:

*Commercial crop time to flowering*.—Approximately 48 to 50 weeks from a rooted cutting to finish in a 12 cm pot.

*Growth habit of peduncle*.—Standard, green leaves, panicle.

*Height (from soil level to top of inflorescence)*.—Approximately 34.0 cm to 39.0 cm.

*Width (measured from leaf tips)*.—About 26.0 cm to 28.0 cm.

*Vigor*.—Moderate.

Leaves:

*Mature leaves*.—Quantity per plant: 7 to 9 leaves are produced before flowering. Length (fully expanded): 13.5 cm to 15.5 cm. Width: 6.5 cm to 7.5 cm. Shape: Oblong. Base shape: Moderately elongated. Apex: Obtuse unequal. Leaf blade angle with the petiole (measured from the horizontal position): Between 25 degrees and 35 degrees. Leaf margin: Entire. Color: Upper surface: RHS 146A. Lower surface: RHS 146B. Texture: Rough upper and lower surface. Thickness: 2.6 mm to 2.7 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—16 to 23.

*Length*.—34.0 cm to 39.0 cm.

*Diameter*.—4.0 mm to 4.4 mm.

*Strength*.—Moderate.

*Aspect*.—Upright to slightly pendant.

*Texture*.—Smooth.

*Color*.—Mix of brown (RHS 200C) and green (RHS 146B).

*Internode length*.—3.0 cm to 4.0 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 150.0 mm to 190.0 mm.

*Flowering time*.—First flowers can be expected 10 to 11 months after planting in a 12 cm (diameter) pot.

*Flower*.—Height: 43.0 mm to 48.0 mm. Diameter: 50.0 mm to 55.0 mm. Depth of lip: 15.0 mm to 18.0 mm.

*Flower longevity*.—On the plant: 8 to 12 weeks.

*Fragrance*.—Absent.

*Flower bud*.—Average size: Medium. Length: 15.0 mm to 17.0 mm. Width: 13.0 mm to 15.0 mm. Shape: Egg shaped. Color: Red-purple (RHS N77B) and slightly green (RHS 145C) at the base.

*Petals*.—Arrangement: Open/free. Shape: Semi-circular. Apex: Obtuse asymmetric. Margin: Entire. Length (from base to tip): 22.0 mm to 24.0 mm. Width: 23.0 mm to 25.0 mm. Color (when fully opened): Upper surface: Basic color: Purple (RHS N78A). Over color: Very small white edge (RHS N155B); very light purple center (RHS 76B); dark red-purple dots (RHS N79C). Lower surface: Basic color: Very light purple (RHS 76B). Over color: Purple-pink edge (RHS N78C); at the base toward the margin white (RHS NN155C) and dark red-purple (RHS N79B).

*Dorsal sepal*.—Shape: Elliptic. Apex: Rounded to slightly emarginated. Margin: Entire. Length (from base to tip): 24.0 mm to 26.0 mm. Width: 15.0 mm to 17.0 mm. Color (when fully opened): Upper surface: Basic color: Purple (RHS N78B). Over color: Very small white edge (RHS N155B); dark red-purple dots (RHS N79B/C). Lower surface: Basic color: Light purple (RHS 76A). Over color: Purple-pink at the base and the tip (RHS N78C).

*Lateral sepals*.—Shape: Ovate. Apex: Obtuse asymmetric. Margin: Entire. Length (from base to tip): 24.0 mm to 26.0 mm. Width: 16.0 mm to 18.0 mm. Color (when fully opened): Upper surface: Basic color: Purple (RHS N78B). Over color: Very small white edge (RHS N155B); light green at the base (RHS 157C) and dark red-purple spots (RHS N79B/C). Lower surface: Basic color: Very light purple (RHS 76B/C). Over color: Diluting dark red-purple spots (RHS N79B) and purple-pink stripe (RHS N78C) toward the tip.

*Labellum (lip)*.—Whiskers: Present. Length of whiskers: 4.0 mm to 6.0 mm. Color of whiskers: Purple (RHS N78A) with white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 12.0 mm to 14.0 mm. Width: 7.0 mm to 9.0 mm. Color: White (RHS NN155C) and slightly yellow (RHS 3A) at the base with few dark red stripes (RHS 187A); red (RHS 59A) and purple (RHS N78A) at the margin.

*Apical lobe*.—Shape: Ovate. Margin: Entire. Length: 17.0 mm to 19.0 mm. Width: 14.0 mm to 16.0 mm. Color: Slightly yellow (RHS 12A) at the base; dark red (RHS 59A/B) and purple (RHS N78A) toward whiskers.

*Callus*.—Average size: Small. Height: 4.0 mm to 5.0 mm. Length: 4.0 mm to 5.0 mm. Width: 3.0 mm to 4.0 mm. Color: Dark red (RHS 187A) and white (RHS NN155C) on sides.

Reproductive organs:

*Column*.—Length: 9.0 mm to 11.0 mm. Diameter: 4.0 mm to 4.3 mm. Color: Purple (RHS N78B).

*Pollinia*.—Quantity: 2. Diameter: 0.7 mm to 0.9 mm. Color: Orange (RHS 24A).

*Ovary*.—Length: 5.0 mm to 7.0 mm. Diameter: 1.5 mm to 1.7 mm.

*Pedicel*.—Length: 26.0 mm to 29.0 mm. Diameter: 1.7 mm to 1.9 mm. Color: Purple (RHS 77B) at the base; very light purple (RHS 76D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGYQAN' differs from female parent plant '10692-03' (unpatented) in that 'PHALGYQAN' has a dark red callus and purple whiskers with white tips, whereas '10692-03' has a yellow, dotted callus and white whiskers. Additionally, 'PHALGYQAN' has a spotted and small center flower pattern and a spotted sepal pattern, whereas '10692-03' has edged flower and sepal patterns.

'PHALGYQAN' differs from male parent plant '01-2078' (unpatented) in that 'PHALGYQAN' has a spotted and small center flower pattern and a spotted sepal pattern, whereas '01-2078' has a flecked flower pattern and a more even sepal pattern.

'PHALGYQAN' is most similar to the commercial *Phalaenopsis* plants named 'PHALFEQBIN' (U.S. Plant Pat. No. 29,615) and 'PHALFASWI' (unpatented). 'PHALGYQAN' differs from the commercial variety 'PHALFEQBIN' in that 'PHALGYQAN' has a spotted and small center flower pattern and a dark red callus with white on the sides, whereas 'PHALFEQBIN' has a spotted and center flower pattern and a dark red callus with yellow tips and white on the sides. Additionally, 'PHALGYQAN' has smaller flowers, shorter whiskers, narrower lateral lobes and wider leaves than 'PHALFEQBIN'.

'PHALGYQAN' differs from the commercial variety 'PHALFASWI' in that 'PHALGYQAN' has a spotted and small center flower pattern and a dark red callus with white on the sides, whereas 'PHALFASWI' has a spotted and edged flower pattern and a dark red callus with yellow on the sides. Additionally, 'PHALGYQAN' has longer whiskers and narrower lateral lobes than 'PHALFASWI'.

I claim:

1. A new and distinct variety of *Phalaenopsis* plant named 'PHALGYQAN', substantially as described and illustrated herein.

* * * * *